United States Patent [19]

Lezzi et al.

[11] Patent Number: 5,296,638

[45] Date of Patent: Mar. 22, 1994

[54] PROCESS FOR PREPARING CARBOXYLATED 2-ALLYL-PHENOLS

[75] Inventors: Alessandro Lezzi, Milan; Arnaldo Roggero, San Donato Milanese; Ugo Pedretti; Cesarina Bonfanti, both of Milan, all of Italy

[73] Assignee: Eniricerche S.p.A., Milan, Italy

[21] Appl. No.: 932,617

[22] Filed: Aug. 20, 1992

[30] Foreign Application Priority Data

Sep. 6, 1991 [IT] Italy .................... MI.91-A/002370

[51] Int. Cl.$^5$ .................... C07C 54/40; C07C 65/01
[52] U.S. Cl. .................... 562/469; 562/475; 560/59; 560/64
[58] Field of Search .................... 562/475, 469

[56] References Cited

FOREIGN PATENT DOCUMENTS 846737  8/1960  United Kingdom .
1235958  6/1971  United Kingdom .

OTHER PUBLICATIONS

Chemical Abstracts No. 16535h, vol. 55, No. 17 (Aug. 21, 1961).
S. Patai, The Chemistry of the Ether Linkage (The Chemistry of Functional Groups), Interscience, N.Y. 1967.
M. P. Fadia et al., Journal Indian Chem. Soc. "Friedel And Crafts Acylation of Ethyl p-Hydroxybenzoath", vol. 32, No. 117 (1955) (pp. 117–119).
CA 107 (21): 191022u 1987.
CA 108 (5): 31987e 1987.

Primary Examiner—Paul J. Killos
Attorney, Agent, or Firm—Shea & Gould

[57] ABSTRACT

An improved process for preparing carboxylated 2-allyl-phenols of general formula (I):

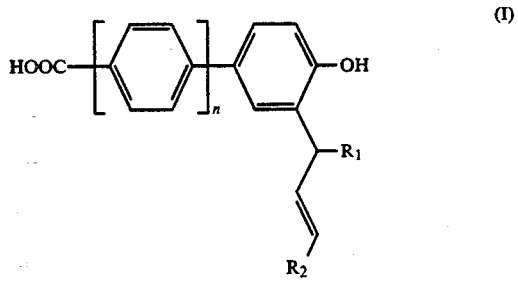

is disclosed, which consists of a first step of simultaneous esterification and etherification of a carboxylated phenol, subsequent rearrangement of the resulting product to yield allyl-carboxylated allyl-phenol and end saponification of the latter into carboxylated 2-allyl-phenol.

7 Claims, No Drawings

PROCESS FOR PREPARING CARBOXYLATED 2-ALLYL-PHENOLS

The present invention relates to an improved process for preparing carboxylated 2-allyl-phenols of general formula (I):

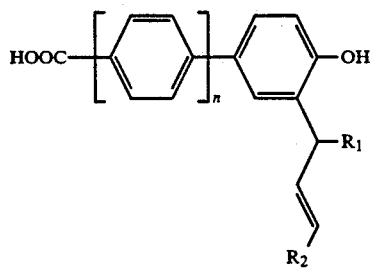

which consists of a first step of simultaneous esterification and etherification of a carboxylated phenol, subsequent rearrangement of the resulting product to yield an allyl-carboxylated allyl-phenol and saponification of the latter into carboxylated 2-allyl-phenol.

Different routes are known in the art in order to prepare carboxylated 2-allyl-phenols.

For example, British patent No. 846,737 discloses the preparation of 4-hydroxy-3-allyl-benzoic acid through the following steps:

(a) esterification, e.g. ethyl-esterification, by reaction of hydroxybenzoic acid with an alcohol in an acidic environment;
(b) allyl-etherification of the resulting ethyl 4-hydroxy-benzoate by reacting the latter with an allyl halide in the presence of sodium in ethanol;
(c) thermal isomerization of the resulting allyl ether of ethyl hydroxy-benzoate, into ethyl 4-hydroxy-3-allyl-benzoate;
(d) end saponification of the resulting ethyl 4-hydroxy-3-allyl-benzoate into the corresponding hydroxy-allyl acid.

Another route also leading to 4-hydroxy-3-allyl-benzoic acids is described by M. P. Fadia et al. in J. Indian Chem. Soc. 32, 117 (1955):

(a) acylation of 4-hydroxybenzoic acid with an acyl halide in the presence of aluminum trichloride;
(b) Fries rearrangement of the resulting acylated 4-hydroxy-benzoic acid into the corresponding 4-hydroxy-3-keto benzoic acid, still in the presence of aluminum trichloride, at about 250° C.;
(c) reduction of the resulting 4-hydroxy-3-keto-benzoic acid into 4-hydroxy-3-allyl benzoic acid, according to methods known from chemical literature.

The first procedure results to be rather complex and requires the use of expensive reactants, such as, e.g., allyl bromide, or dangerous reactants, such as sodium metal.

The second procedure requires a smaller number of steps, but the yields thereof are poor and the recovery of the reaction products is particularly expensive.

The present Applicant found now an improved process for preparing carboxylated 2-allyl-phenols which only requires three reaction steps, enables the reaction products to be easily recovered, and makes it possible less toxic and cheaper reactants to be used.

In accordance therewith, the present invention relates to a process for preparing carboxylated 2-allyl-phenols of general formula (I):

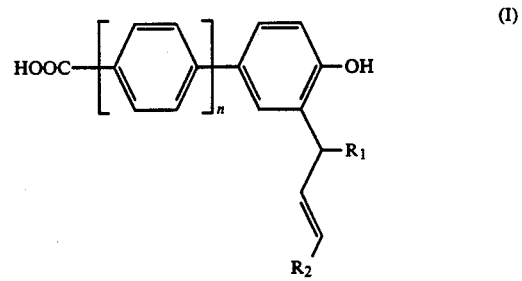

wherein:

n is zero or 1, $R_1$ and $R_2$, which may be the same or different from each other, are hydrogen or a $C_1$–$C_2$ alkyl radical, which process is characterized by the following steps:

(a) simultaneous allyl-esterification and allyl-etherification of a hydroxy-carboxy acid of general formula (II):

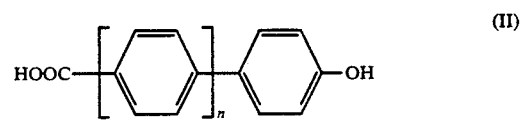

wherein n is either zero or 1, by means of the reaction, in the presence of bases, of said hydroxy-carboxy acid with an allyl halide of general formula (III)

$$X\text{—}CHR_2\text{—}CH\text{=}CHR_1 \qquad (III)$$

wherein $R_1$ and $R_2$ have the above explained meaning and X represents either Cl or Br;

(b) thermal rearrangement of the resulting allyl-ether allyl-ester into allyl-carboxylated 2-allyl-phenol;

(c) end saponification of said allyl ester into carboxylated 2-allyl-phenol of formula (I).

The sequence of reaction steps can be schematically shown as follows:

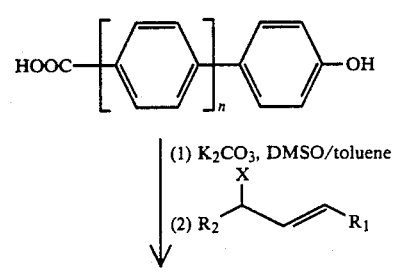

3

-continued

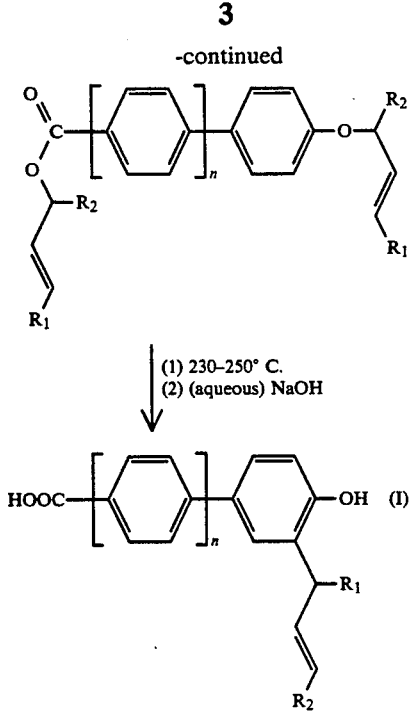

In the preferred form of practical embodiment of the present invention, n is zero and $R_1$ and $R_2$ are hydrogen, and consequently the product of general formula (I) is 4-hydroxy-3-allyl-benzoic acid.

According to a preferred form of practical embodiment of the present invention, the first step is carried out by reacting the hydroxy-carboxy acid, preferably diluted with a suitable solvent, with an alkali metal or alkaline-earth metal hydroxide or carbonate, preferably sodium or potassium carbonate, in a molar ratio of carbonate/hydroxy-carboxy acid higher than 2 and preferably comprised within the range of from 2.1 to 4, with the reaction mixture being heated, so as to eliminate, by means of techniques known from the prior art, any formed water, and with the allyl halide being subsequently added to the reaction mixture, heated at approximately 40°-80° C. and the resulting allyl-ester allyl-ether being recovered, preferably by extraction.

The second reaction step is advantageously carried out by heating the allyl-ester allyl-ether to a temperature comprised within the range of from 200 to 280° C., preferably of from 220° to 260° C., in the presence of a heat stabilizer, in order to prevent the product from undergoing a radicalic degradation, for a time comprised within the range of from 2 to 6 hours, and with the resulting allyl-carboxylated 2-allyl-phenol being recovered.

In the third reaction step, said allyl-carboxylated 2-allyl-phenol is saponified by treatment with an aqueous solution of a strong base and subsequent acidification.

The resulting carboxylated 2-allyl-phenol of general formula (I) can be used as such as a (co)monomer for polyesters, e.g. for polymeric liquid crystals, or it can be hydrogenated to yield carboxylated 2-alkyl-phenol. Also the latter can be used as a (co)monomer for polyesters.

The following experimental examples are supplied in order to illustrate the present invention in greater detail.

4

EXAMPLE 1

(A) Synthesis of the allyl ester of 4-(2-propen-1-yl)oxy-benzoic acid

To a reaction flask equipped with a Dean-Stark head, 10 g of 4-hydroxy-benzoic acid, 25 g of potassium carbonate, 150 ml of dimethyl-sulfoxide and 50 ml of toluene are charged. The reaction mixture is heated up to about 150° C. for approximately 4 hours: from the Dean-Stark head the water/toluene azeotrope and virtually any residual toluene are collected. The reaction mixture is then cooled to approximately 60° C., and at that temperature 11.2 g of allyl chloride is added during about 30 minutes. The reaction is stopped after 2 hours, the cooled mixture is poured into water, and the aqueous phase is repeatedly extracted with ether. By concentrating the ethereal phase, the allyl ester of 4-(2-propen-1-yl)-oxy-benzoic acid was recovered.

The $^1$H-N.M.R. and I.R. spectra of the resulting product are reported in the following.

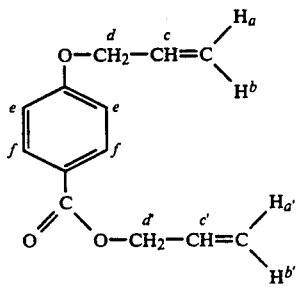

$^1$H-N.M.R. (TMS): a,a': 5.3 (d); b,b': 5,4 (d); c,c': 6.1 (m); d: 4.55 (d); d': 4.8 (d); e: 7.0 (d); f: 8.0 (d) ppm.*

* d=doublet; m=multiplet.

FT-IR: 1718 (C=O); 1650 (C=C); 1270 [—C-(O)—OR]; 1170 (—C—OR); 997 (—CH=); 932 (=CH$_2$) cm$^{-1}$.

(B) Synthesis of the allyl ester of 4-hydroxy-3-(2-propen-1-yl)-benzoic acid

To a reaction flask 10 g of the allyl ester of 4-(2-propen-1-yl)-oxy-benzoic acid, prepared as disclosed hereinabove, and about 0.1 g of a hindered phenol, selected from among commercial products, to prevent degradation reactions of radicalic type are charged under an inert atmosphere. The reaction mixture is then heated at 230°-250° C. for approximately 4 hours. The reaction mixture is cooled, and the product is dissolved in ethyl ether and is treated with decolurizing charcoal. After filtration, and evaporation of the solvent, the allyl ester of 4-hydroxy-3-(2-propen-1-yl)-benzoic acid was obtained with a yield of 90%, based on the starting product.

(C) Synthesis of 4-hydroxy-3-(2-propen-1-yl)-benzoic acid 15 g of the allyl ester of 4-hydroxy-3-(2-propen-1-yl)-benzoic acid, prepared as disclosed hereinabove, and an aqueous 4M solution of sodium hydroxide (200 ml) are charged to a flask. The resulting mixture obtained in that way is heated up to 100° C. for about 2 hours. After cooling, to the aqueous solution concentrated hydrochlorid acid was added until a pH value in the acidic range was obtained. The reaction product, insoluble at acidic pH, is recovered by filtration and then is repeatedly washed with water and dried.

The obtained yield was of 70%, based on the starting product.

In the following, the ¹H-N.M.R. and I.R. spectra of so obtained 4-hydroxy-3-(2-propen-1-yl)-benzoic acid

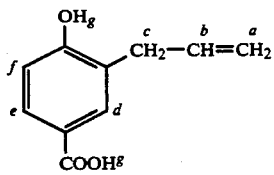

are reported.

¹H-N.M.R. (TMS): a: 5.1 (m); b: 6.0 (m); c: 3.42 (d); d: 7.86 (d); e: 7.83 (d); f: 6.96 (d); g: 9.78 (bs) ppm*

*d=doublet;
m=multiplet;
bs=broad singlet.

FT-IR: 1653 (C=O); 1194 (C—OH); 995 (—CH=); 910 (=CH$_2$) cm$^{-1}$.

We claim:

1. A process for preparing a carboxylated 2-allyl-phenol of formula (I):

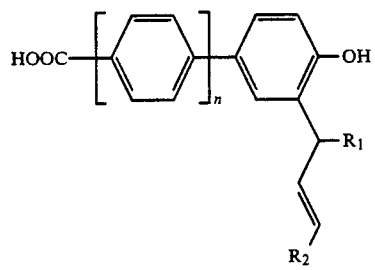

wherein:

n is zero or 1,

R$_1$ and R$_2$, which can be the same or different, are hydrogen or C$_1$-C$_2$ alkyl, comprising:

(a) simultaneously allyl-esterifying and allyl-etherifying a hydroxy-carboxy acid of formula (II):

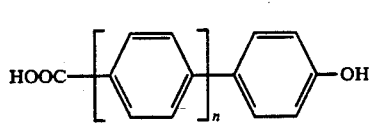

wherein n is zero or 1, with an allyl halide of formula (III):

X—CHR$_2$—CH=CHR$_1$ wherein R$_1$ and R$_2$ are as defined above and X is Cl or Br, by reacting the hydroxy-carboxy acid with an alkali metal or alkaline-earth metal carbonate in a molar ratio of carbonate/hydroxy-carboxy acid of greater than 2 while heating the reaction mixture to remove water and subsequently adding the allyl halide to the reaction mixture at 40°-80° C. to produce an allyl-ester allyl-ether of the hydroxy-carboxy acid and separating the allyl-ester allyl-ether from the reaction mixture;

(b) heating the allyl-ester allyl-ether at a temperature of 200° to 280° C. for a period of from 2 to 6 hours in the presence of a heat stabilizer to thermally rearrange the allyl-ester allyl-ether to an allylcarboxylated 2-allyl-phenol, and recovering the allylcarboxylated 2-allyl-phenol; and (c) saponifying the allylcarboxylated 2-allyl-phenol by treatment with a strong base and subsequent acidification to produce the 2-allyl-phenol of formula (I).

2. Process for preparing carboxylated 2-allyl-phenols according to claim 1, wherein n is zero and R$_1$ and R$_2$ are hydrogen.

3. A process for preparing carboxylated 2-allyl-phenols according to claim 1, wherein, in step (a), the hydroxy-carboxy acid is diluted with a suitable solvent.

4. A process for preparing carboxylated 2-allyl-phenol according to claim 1, wherein, in step (a), the alkaline metal or alkaline-earth metal hydroxide or carbonate is sodium or potassium carbonate.

5. A process for preparing carboxylated 2-allyl-phenol according to claim 1, wherein, in step (a), the molar ratio of carbonate/hydroxy-carboxy acid is from 2.1 to 4.

6. A process for preparing carboxylated 2-allyl-phenol according to claim 1, wherein, in step (a), the resulting allyl-ester allyl-ether is recovered by extraction.

7. A process for preparing carboxylated 2-allyl-phenol according to claim 1, wherein, in step (a), the temperature is from 220° to 260° C.

* * * * *